(12) United States Patent
Giannou

(10) Patent No.: US 6,405,912 B2
(45) Date of Patent: *Jun. 18, 2002

(54) PROTECTIVE CASE FOR CARRYING A FRAGILE OBJECT

(75) Inventor: Martha Giannou, Manotick (CA)

(73) Assignee: Zoni Inc. (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/410,081

(22) Filed: Oct. 1, 1999

(30) Foreign Application Priority Data

Oct. 20, 1998 (CA) .................................. 2251863

(51) Int. Cl.⁷ .................................. A45C 1/04
(52) U.S. Cl. .................. 224/679; 224/233; 224/660; 224/682; 224/235; 224/240; 224/901.6
(58) Field of Search .................. 224/178.7, 195, 224/223, 660, 663, 678, 679, 682, 235, 236, 240, 241, 901.6; 215/306; 220/375

(56) References Cited

U.S. PATENT DOCUMENTS

| | | | | |
|---|---|---|---|---|
| 2,399,040 A | * | 4/1946 | Karle | 224/660 X |
| 3,445,046 A | * | 5/1969 | Wilson | 224/240 X |
| 4,018,371 A | * | 4/1977 | George | 224/660 X |
| 4,244,499 A | | 1/1981 | Adams | 224/224 |
| 4,399,934 A | | 8/1983 | Dupont | 224/240 |
| 4,757,894 A | | 7/1988 | Schreckenstein | |
| 4,796,790 A | * | 1/1989 | Hamilton | 224/253 |
| 4,942,991 A | | 7/1990 | Lyons | 224/196 |
| 5,002,214 A | | 3/1991 | Caranci | 224/252 |
| 5,048,734 A | * | 9/1991 | Long | 224/148.7 |
| 5,078,267 A | | 1/1992 | Wright | |
| 5,135,144 A | | 8/1992 | Blakely et al. | 224/240 |
| 5,240,158 A | | 8/1993 | Walsh | |
| 5,392,974 A | | 2/1995 | Johnson-Rabbett | 224/253 |
| 5,470,001 A | * | 11/1995 | Konchan | 224/240 X |
| 5,577,653 A | | 11/1996 | Bieker | 224/684 |
| 5,740,951 A | * | 4/1998 | Jack | 224/148.3 |
| 5,779,122 A | | 7/1998 | Martinelli | 224/683 |
| 5,864,289 A | * | 1/1999 | Tiemann | 224/610 X |
| 5,931,363 A | * | 8/1999 | Ammons, Jr. | 224/602 |

* cited by examiner

*Primary Examiner*—Stephen K. Cronin
(74) *Attorney, Agent, or Firm*—Killworth, Gottman, Hagan & Schaeff, L.L.P.

(57) ABSTRACT

A protective case to be worn by an individual for carrying a medical device that may be required in case of allergic or asthmatic reactions or diabetic reactions. The case includes a rigid receptacle to protect the medical device. The case can be worn on a person's belt or it may be permanently fixed to a belt or a band that can be worn around the waist, an arm or a leg. For a standard syringe, the receptacle comprises an elongated, rigid cylindrical tube which fits closely about the syringe. The receptacle further includes an open end that is covered by a cap that can be readily removed to provide easy access to the syringe inside the tube and which protects the syringe from contamination. The case is unobtrusive in appearance and does not hamper the individual's movements thus allowance it to be worn at all times.

9 Claims, 7 Drawing Sheets

PROTECTIVE CASE FOR CARRYING A FRAGILE OBJECT

FIELD OF THE INVENTION

The present invention relates to protective cases and in particular to a protective case to be worn by an individual for carrying a fragile object.

BACKGROUND OF THE INVENTION

There are emergency situations when it is necessary for an individual to have a medical device close at hand. In particular, people with potentially fatal allergic or asthmatic reactions, with diabetes, or other similar conditions, are required to have immediate access to medical devices such as syringes with medicated serum which must be administered quickly. One way to assure immediate access to such devices is to have the individual carry the necessary medical equipment with him or her at all times.

The devices such as syringes are usually fragile and must be well protected against breakage particularly when they are being carried during all activities. Additionally, they must also be protected against all contaminants such as water and dirt. Further, as pain or panic can impede a person from reacting during an emergency situation in the same manner as under normal circumstances, it is necessary for the individual or someone helping to have easy access to the medical device. It is therefore desirable for the individual to wear the medical device on his or her person on the outside of the clothing where it is easily accessible and also highly visible so that the person helping the individual in an emergency situation would not need much guidance to find it. Comfort and appearance are therefore important in order to avoid having the individual remove the device during certain activities.

Adults carry their day-to-day use items in a briefcase or a purse. Students currently carry their school needs in back packs. However, in both of the above cases, they are usually set aside while driving, while working and especially while doing physical activities such as sports.

Another accessory commonly used by all age groups is the fanny pack. However, the fanny pack is found by adults to be too obtrusive particularly during sporting activities and formal occasions. For children and adolescents they are too bulky in appearance and hamper their freedom of movement. Some children find themselves the target of jibes and taunts from their peers while wearing them. Furthermore, the fanny pack is not rigid enough to protect a fragile object such as a syringe against damage from external jolts and blows.

The above situations often result in the medical device not being close at hand or difficult to find when it is urgently needed, or, worse yet, the device may be found to be damaged when the serum is to be administered.

The need for a protective case that overcomes the above disadvantages is therefore apparent.

SUMMARY OF THE INVENTION

It is an object of the present invention to provide an improved protective case to be worn by an individual for carrying a fragile object.

The present invention is directed to a protective case which comprises a receptacle having a wall of rigid material that defines a cavity for the fragile object and an opening for taking the fragile object out of the cavity. The receptacle further includes a removable cover which closes the cavity opening. The case further includes means for securing the receptacle to the individual.

In accordance with another aspect of the invention, two or more receptacles may be fixed together such that two or more fragile objects may be carried by an individual.

In accordance with a further aspect of the invention, the configuration of the cavity interior restricts the movement of the fragile object within the cavity to prevent it from being damaged; the interior of the cavity may be similar in size and shape as the fragile object.

In accordance with another aspect of the invention, the cover is adapted to seal the opening when closed to prevent the interior of the cavity from becoming contaminated and the opening in the cavity is adapted to allow the fragile object to move freely out of the cavity when the cover is removed.

In accordance with yet another aspect of the present invention, the receptacle may be insulated to prevent the fragile object or its contents from being damaged.

In accordance with a further aspect of this invention the receptacle may be secured to the individual by mounting it on a belt or band that can be worn by the individual, or alternately, one or more belt loops may be fixed to the receptacle so that it can be placed on a waist belt or a band.

In accordance with a more specific aspect of the present invention, the protective case receptacle for carrying a medical syringe may comprise a wall of rigid material defining an elongated, tubular cavity for receiving the syringe in a close fit. One end of the tubular cavity is sealed such as by a rigid stopper fixed to the end of the tubular cavity to prevent accidental puncturing by the syringe needle. An opening at the other end of the tubular cavity enables the syringe to be freely taken out of the cavity. The open end of the cavity may further be tapered to receive a cap that fits over the open end.

In accordance with another aspect of this invention, the case securing means may include a flexible holder adapted to form a tight fit around the rigid wall of the receptacle and a loop forming member fixed to the flexible holder. The loop forming member may be a waist belt or one or more belt loops for mounting on a belt or band.

In accordance with a further aspect of this invention, the cap may be connected to the holder by an elasticized strap and one end of a flexible strap may also be fixed to the cap. The other end of the flexible strap may be used to pull the cap open or to hold the cap closed by being detachably fixed to the side of the holder.

In accordance with another specific aspect of the present invention, the rigid cavity wall is molded. The cavity wall may include a groove formed about its outer surface near the opening for receiving a ridge formed about the inner surface of the cap which is snapped into place when the cap is placed over cavity opening. The molded cavity wall may further include two projections each having a slit into which a belt is fixed whereby the case may be secured to an individual.

Other aspects and advantages of the invention, as well as the structure and operation of various embodiments of the invention, will become apparent to those ordinarily skilled in the art upon review of the following description of the invention in conjunction with the accompanying drawings.

BRIEF DESCRIPTION OF THE DRAWINGS

The invention will be described with reference to the accompanying drawings, wherein.

DETAILED DESCRIPTION OF THE INVENTION

Figure 1:
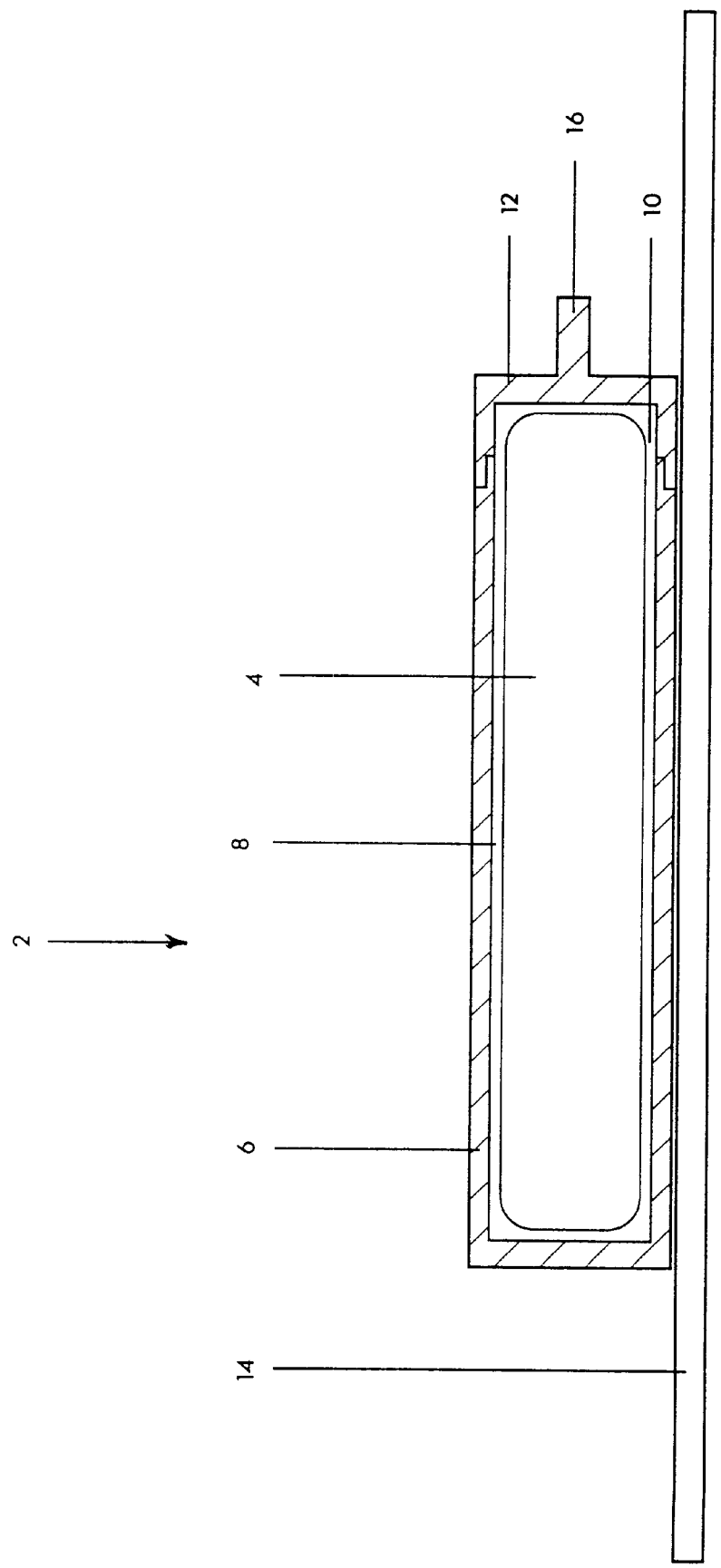
FIG. 1 presents a schematic view of a protective case in accordance with the present invention.

FIG. 1 schematically depicts a protective case 2 to be worn by an individual to carry a fragile object 4, in accordance with the present invention. The case 2 comprises a receptacle 6 and means 14 for securing the receptacle 6 to the individual.

The receptacle 6 comprises a defining wall of rigid material such as plastic, metal or the like. The rigidity of the wall is meant to protect the fragile object 4 from external pressure or twisting forces that may be exerted accidentally during normal use. The wall of rigid material forms a cavity 8 into which the fragile object 4 is placed. The cavity is closely fitted to the object 4 so that the size of the case 2 is minimized. In this way, it will be non-obtrusive in appearance and it will not hamper the movement of the wearer. Additionally, the close fit restricts the movement of the fragile object 4 within the cavity 8, thus preventing breakage of the object 4 that might occur as a result of it hitting the interior walls of the cavity, during wear, when the case 2 is jotted. The degree of protection of the object 4 in this sense, can be further increased by adding cushioning pads inside the cavity 8.

The rigid wall of the receptacle 6 further includes at least one opening 10, for the insertion of the object 4 into the cavity 8 and for it to be taken out of the cavity 8. Under certain circumstances it may be desirable to have an insertion opening that differs from the opening used to take out the object 4, however, generally a single opening would suffice. The opening 10 is provided with a cover 12 which covers the opening 10 to hold the fragile object 4 inside the cavity 8 and which may be removed to allow the object 10 to be taken out of the cavity 8. The cover 12 is also preferably manufactured from a rigid material, for enhancing the protective function of the case 2. The cover 12 can be a flap, stopper, cap, or any other suitable cover known in the art. In the embodiment in FIG. 1, the opening inserting and for taking out the object 4 are the same and a cap 12 is used to cover the opening 10.

In the embodiment of FIG. 1, the cap 12 completely surrounds the opening 10, providing a tight seal against contamination of the cavity, for example from dirt and water. A pull-out member 16 is attached to the cap 12, to facilitate the removal of the cap 12, particularly under emergency conditions. The pull out member 16 can be a small pin such as in FIG. 1, a strap or any other means that is easy to grip. Alternatively, the cap 12 can be provided with an easy to grip surface on its exterior.

The securing means 14 includes a loop forming member, to which the receptacle 6 is attached. The loop forming member may take the form of a band or belt to fit around an individual's waist, wrist, arm or leg. Preferably, the length of such a belt or band would be adjustable. Alternatively, the loop forming member may be one or more small flexible loops that can be slid about a waist belt.

Figure 2:
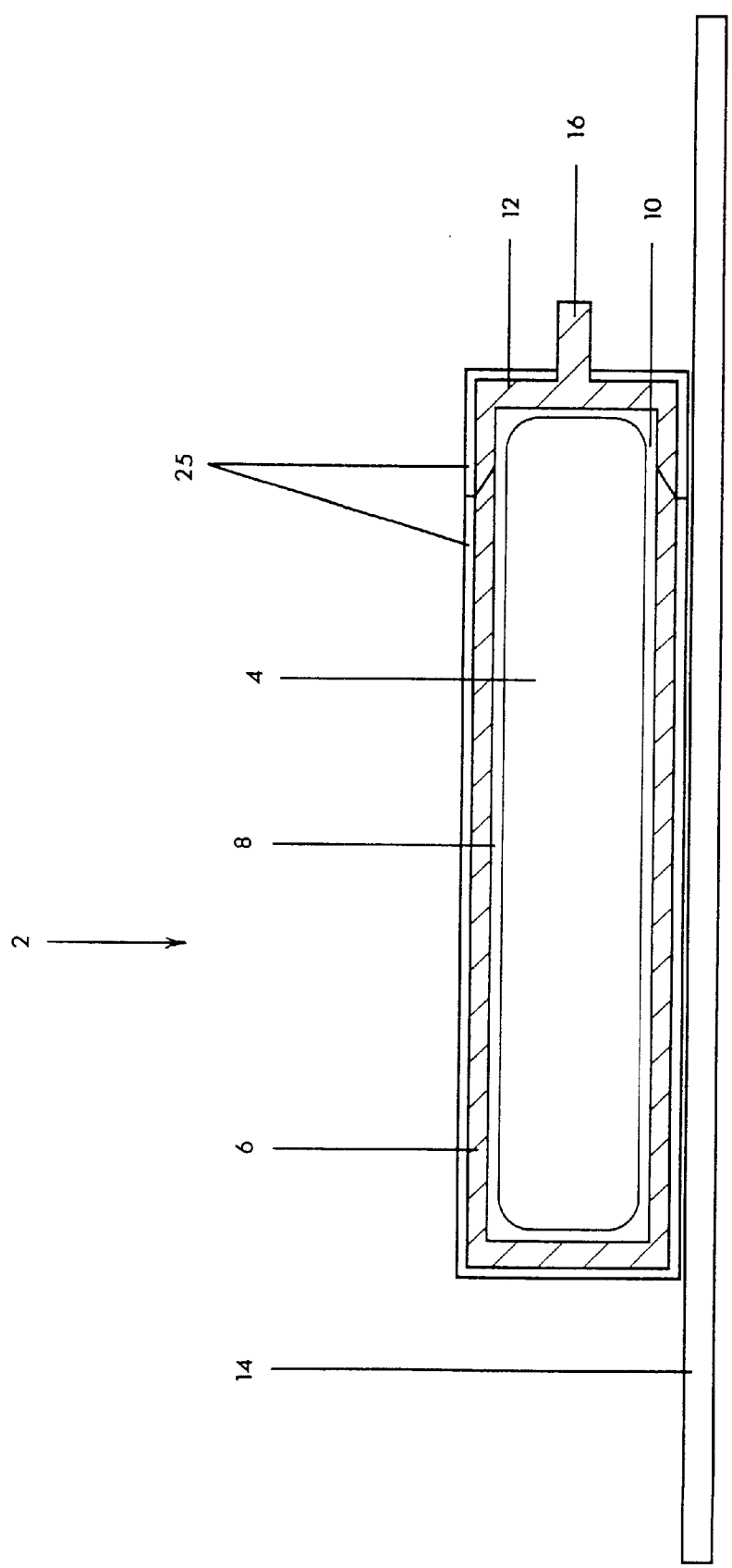
FIG. 2 presents a schematic view of an insulated protective case in accordance with the present invention.

In the embodiment in FIG. 2, the protective case 2 is provided with thermal insulation 25 for preventing the fragile object 4 from being damaged due to exposure to temperatures that are higher or lower than an acceptable range, or to temperature variations. In FIG. 2, the thermal insulation 25 includes a layer of insulating material such as Solary™, attached to the exterior of the receptacle 6 and of the cap 12. Alternatively, a layer of insulating material can be attached to the interior of the receptacle 6 and of the cap 12.

In the preferred embodiment depicted in FIGS. 3 to 6, a protective case 30 carries a medical syringe, such as an Epipen, which is an emergency injector with epinephrine used for anaphylaxis shock, or a Novolin-Pen, for injecting insulin, used by a person with diabetes.

Figure 3:
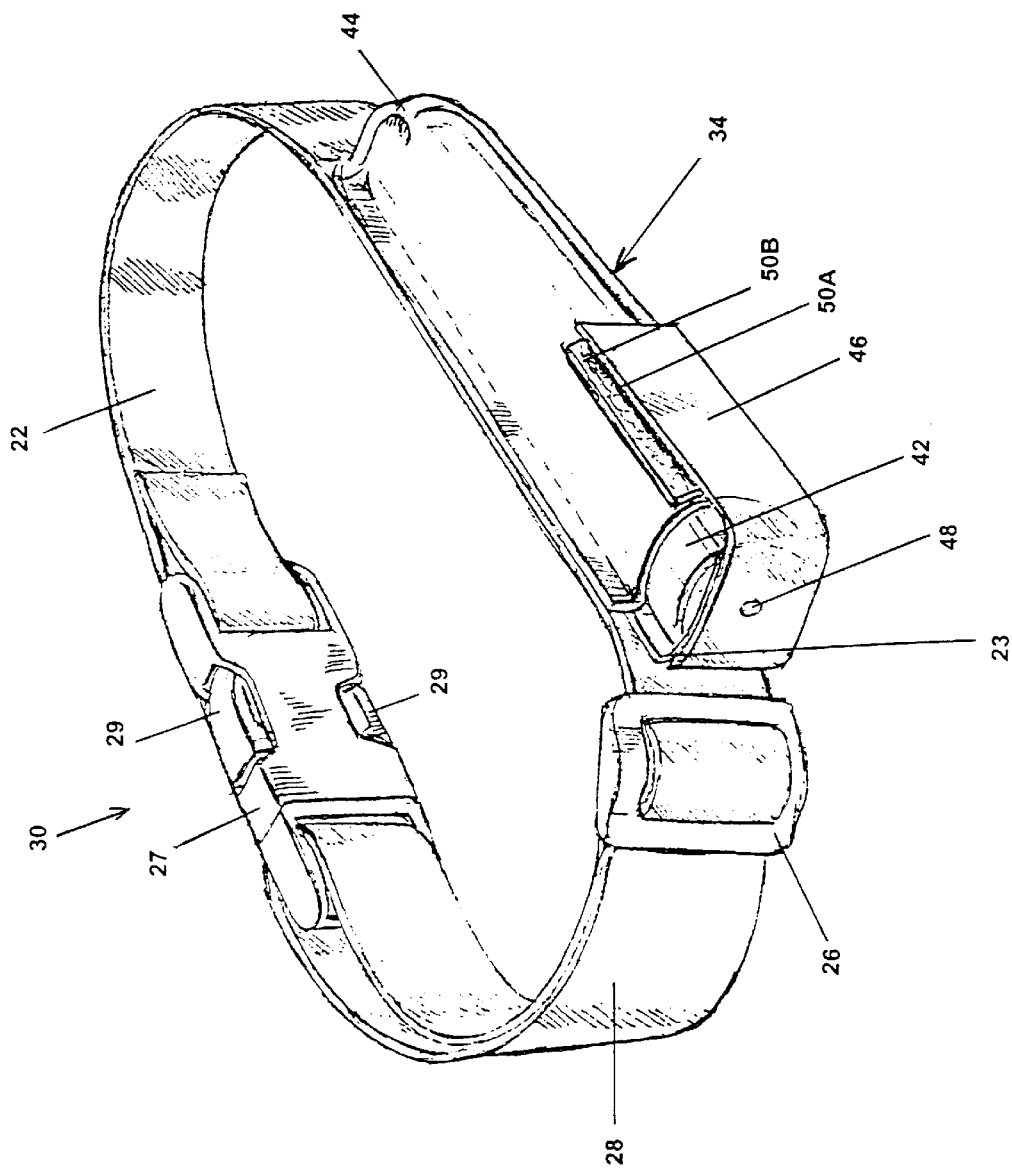
FIG. 3 presents a perspective view of a protective case in accordance with a preferred embodiment of the invention.

FIG. 3 shows a perspective view of the protective case 30 for the emergency injector. The protective case 30 comprises a receptacle 34 attached to a belt 22.

Figure 4:
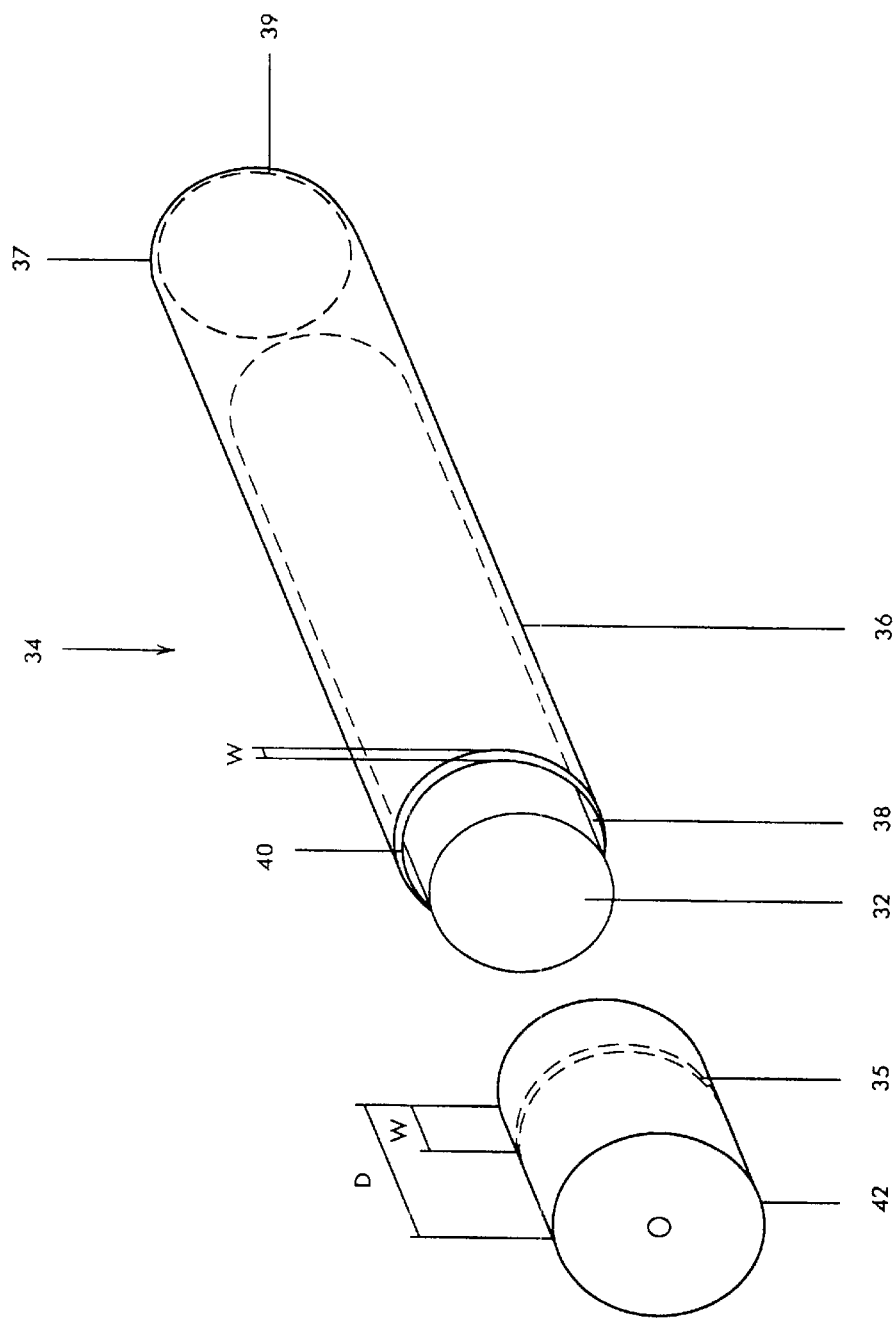
FIG. 4 presents a perspective view of the receptacle for the protective case shown in FIG. 3.

Referring to FIG. 4, the receptacle 34 comprises a cylindrical rigid tube 36, manufactured from a durable material such as PVC. The size of the tube 36 is determined by the size of the emergency injector 32 that it has to carry. The tube 36 must be sufficiently large to receive a standard syringe 32, but small enough such that it is non-obtrusive in appearance and does not hamper movement of the wearer of the case. For standard Epipens, the tube 36 is approximately 5⅜ inches long with an inside diameter of ¾ inches and ⅛ inch thick walls. Preferably, the tube 6 is designed to withstand approximately 1000 lbs of pressure.

The cylindrical tube 36 is permanently plugged at end 37 with a heavy duty PVC stopper 39. The stopper 39 is required in case the syringe 32 discharges accidentally within the tube 36 in order to prevent the syringe 32 needle from emerging from the tube 36.

In the embodiment depicted in FIG. 4, the tube 36 is slightly shorter than the syringe 32. This feature allows the syringe 32 to be easily taken out of the tube 36. It is also preferred that the syringe 32 can only be inserted through the opening 38 in only one direction such that the needle end of the syringe 32 rests at the plugged end 37 of the tube 36. A rigid cap 42 covers the opening 38 of the tube 36. In the preferred embodiment, the cap is manufactured from a rigid plastic material, which is slightly elastic. The open end 40 of the tube 36 is slightly tapered or bevelled on its external surface. Tapering allows the plastic cap 42 to be pressed onto the end 44 of tube 36, in addition to keeping the syringe 32 in place. The cap 42 protects the syringe 32 from contamination, such as by dirt and moisture. The tapered surface of the tube 36 has a width W, sufficiently large to confer a good gripping effect when the cap 42 is press fitted over it. The depth D of the cap 42 is greater than the width W of the tapered surface. Preferably, the cap 42 includes an internal circular ridge 35 at a distance W from the rim of the cap 42 that slides over the tube 36. The internal ridge 35 prevents the cap 42 from sliding over the tube 36 further than the distance W, thus preventing accidental breakage of the syringe 32 from having the cap 42 slide too far over the tube 36.

Referring also to FIG. 3, the tube 36 is held in place by a strong flexible material such as leather, positioned along the belt 22, forming a sheath 44 for the tube 36 and double stitched to the belt 22 such as to provide a tight fit for the tube 36. For enhancing the resistance to tear, the sheath 44 is triple stitched at one end and open on the other end. The tube 36 is inserted into the sheath 44 and glued in place.

The cap 42 is attached to the belt 22 via a combination of materials designed to provide easy access to the syringe 32. One end of an elasticized strap 23 is sewn to the belt 22 near the open end of sheath 44. The other end of the elasticized strap 23 is attached to the cap 42 where it is stitched to a nylon webbing 46 which forms a pull-out strap for the cap 42 to remove the cap 42 from the opening 40. The elasticized material 23 and the nylon webbing 46 form are connected to the cap 42 with a rivet 48.

On the outside of the sheath 44, towards the open end 40 of the tube 36, there is sewn the female portion 50B of a hook and loop type strip 50. Correspondingly, on the nylon webbing forming the pull-out strap 46, there is sewn the male portion 50A of the hook and loop strip 50, which secures the cap 42 in place over the end of the tube 36.

In this embodiment of the invention, the belt 22 comprises a nylon webbing 28 which wraps around a person's waist. The webbing 28 may come in different lengths and further includes a tie 26 that allows it to be adjustable to fit people of different sizes. The belt 22 further has a buckle 27 with two quick release tabs 29. It is made of durable high-grade plastic.

In the embodiment presented in FIG. 3, the sheath 44 is sewn lengthwise directly onto the belt 22 webbing 28 at a location which places the tube 36 in front of the abdomen of the person wearing the belt, and the plastic buckle 27 is in the back of the person.

In a further embodiment, the protective case, illustrated in FIG. 3, may include additional pouches or holders fixed to the belt 22. These pouches can be used to carry Benadryl™ tablets, necessary in case of asthmatic reactions, or small water containers.

Figure 5:
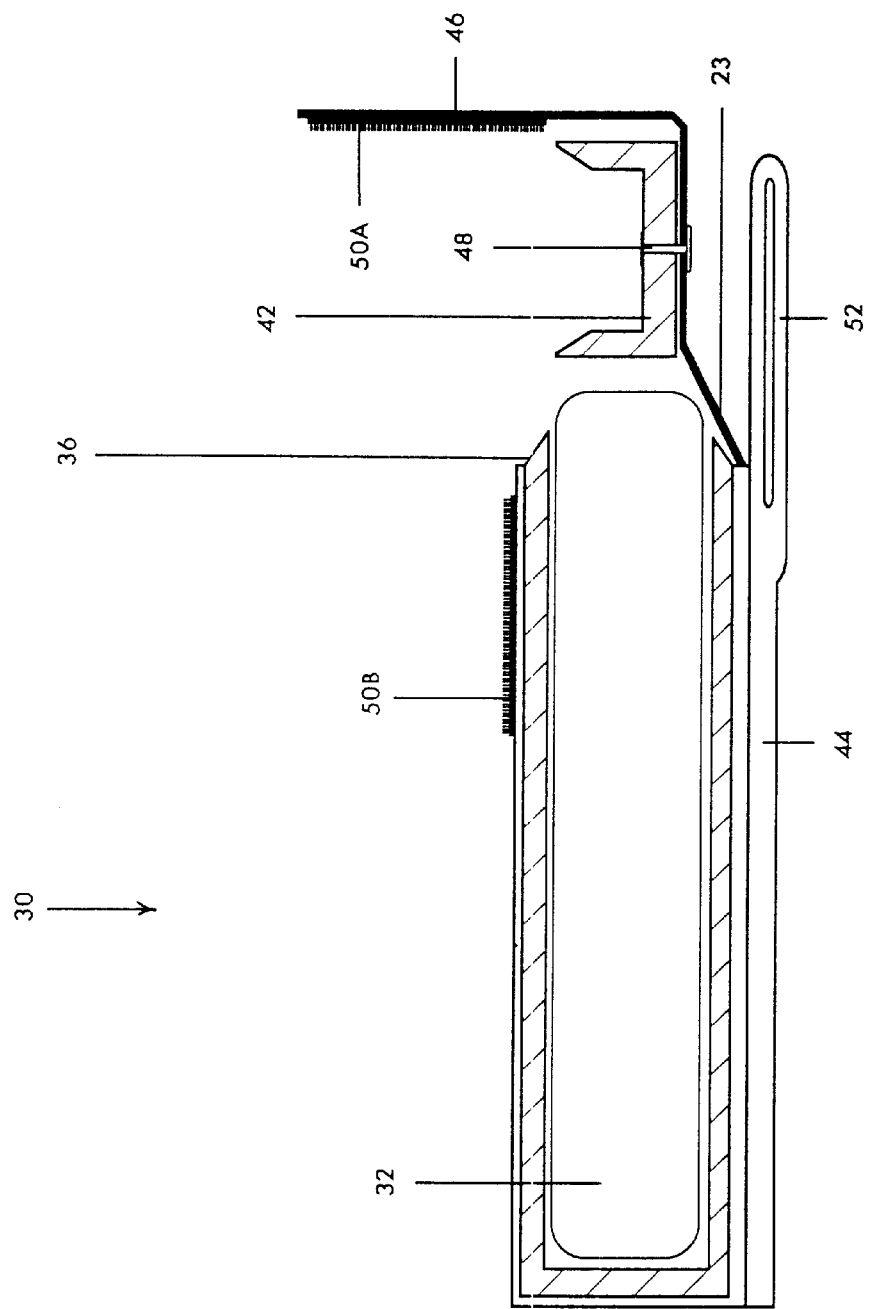
FIG. 5 presents a side view of a protective case with a belt loop in accordance with an embodiment of the invention.

FIG. 5 depicts an alternate embodiment of the invention, in which a loop 52 is fixed to the sheath 44 to allow the case 30 to be carried on a person's existing belt. The protective case 30 is thus mounted vertically with the quick release cap 42 on the top. Similarly, two or more loops may be fixed to the sheath 44 across the width of the sheath 44 such that the loops would slip over a persons belt in the horizontal direction.

Figure 6:
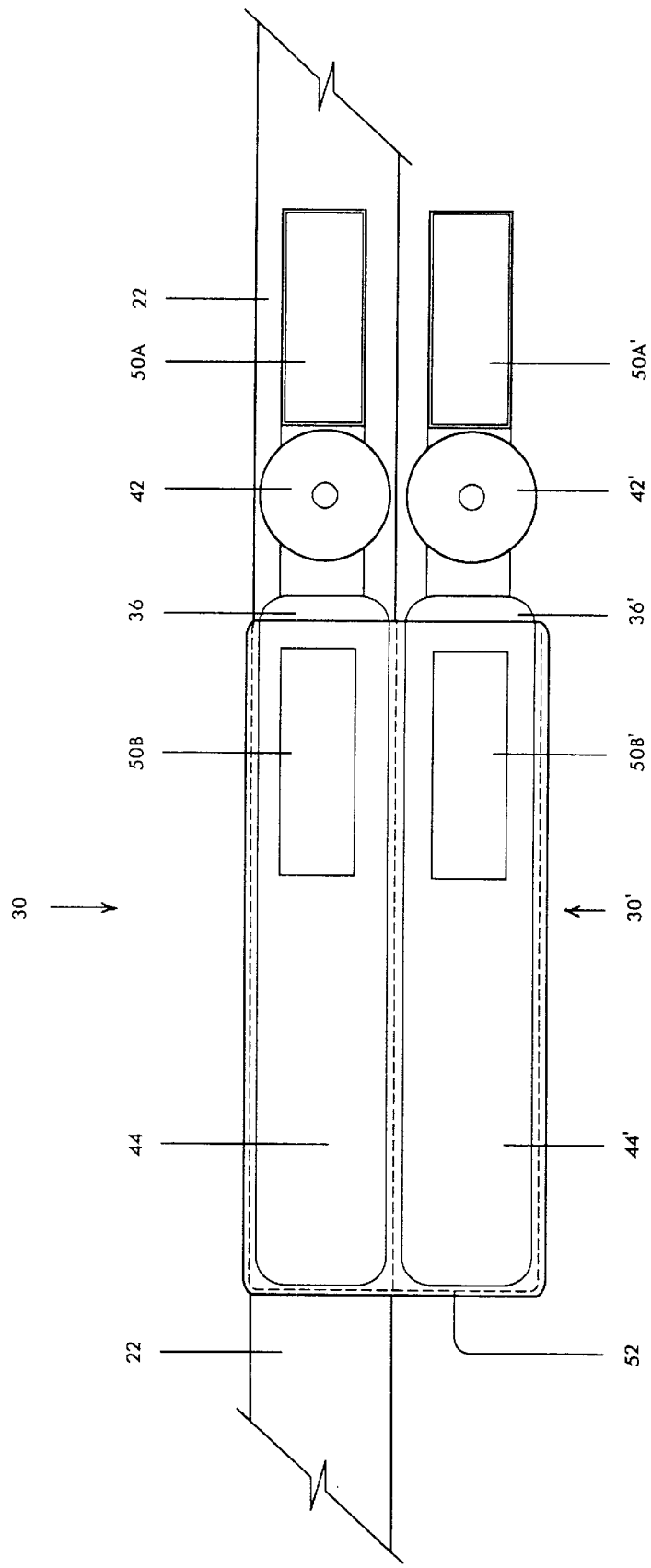
FIG. 6 presents a top view of a protective case having two receptacles, in accordance with an embodiment of the invention.

FIG. 6 illustrates an arrangement in accordance with another embodiment of the invention in which two protective cases 30 and 30' are mounted side by side to carry two different syringes. The protective cases 30 and 30' comprise two tubes 36 and 36', each tube 36, 36' being similar to the tube 36 illustrated in FIGS. 3 and 4. The sheath 44 for tube 36 is attached to a nylon webbing forming a belt 22, as in FIG. 3. The sheath 44' for tube 36' is formed by attaching a flexible material lengthwise to a nylon webbing 52 having approximately the same length as the tube 36'. The sheaths 44 and 44' are attached together by sewing the nylon webbing 52 to the nylon webbing forming the belt 22. It will be appreciated by a person skilled in the art that with respect to this embodiment that further receptacles may be joined together in a similar manner.

Figure 7:
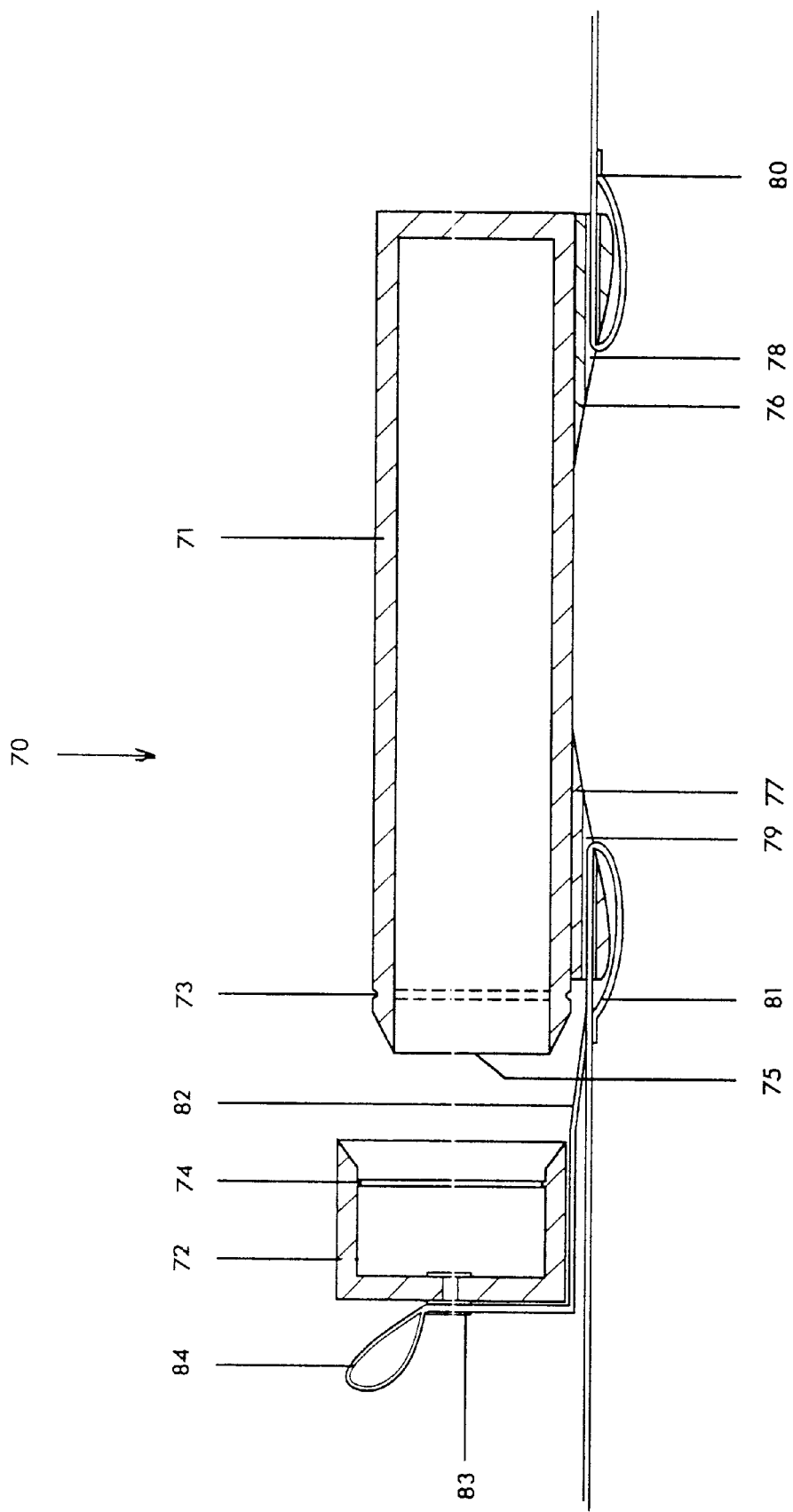
FIG. 7 illustrates in cross-section a moulded protective case in accordance with an embodiment of the present invention.

The case 70 illustrated in FIG. 7 comprises a receptacle having a molded tubular cavity 71 and a cap 72 that fits over opening 75 of cavity 71. The cavity 71 is made of rigid material which is closed at one end and has an opening 75 at the other end for placing a fragile object such as a syringe into the cavity. The opening 75 end of the cavity 71 is further tapered to receive the cap 72 and includes a groove around the circumference of the cavity 71 at the opening 75 end to receive a ridge 74 which is moulded on the interior of the cap 72. When the ridge 74 snaps into the groove 73, the opening 75 is sealed, preventing contamination from entering into cavity 71. In addition, the ridge 74 and groove 73 act as a stop such that the cap 72 will not push further onto the cavity 71. The molded cavity 71 further has projections 76,77, each having a slit 78, 79 respectively. A belt webbing 80 is looped back on itself through slit 78 and sewn together. A further belt webbing 81 is also looped on itself through slit 79 and sewn together. The remainder of the belt webbings 80 and 81 form a belt as in FIG. 3. One end of an elasticized strap 82 is sewn to the belt webbing 81 and the other end is sewn to a short strap 84 and together they are fixed to the cap 72 by a rivet 83. The loose end of strap 84 is used to pull the cap 72 to remove it from opening 75.

While the invention has been described according to what is presently considered to be the most practical and preferred embodiments, it must be understood that the invention is not limited to the disclosed embodiments. Those ordinarily skilled in the art will understand that various modifications and equivalent structures and functions may be made without departing from the spirit and scope of the invention as defined in the claims. Therefore, the invention as defined in the claims must be accorded the broadest possible interpretation so as to encompass all such modifications and equivalent structures and functions.

What is claimed is:

1. A protective case to be worn by an individual for carrying a medical syringe, the case comprising:
   a receptacle for holding the syringe comprising a cavity capable of being sealed against moisture, dirt and contaminants;
   a flexible holder for enclosing said receptacle;
   a removable cap for sealing said cavity; said removable cap being secured to said flexible holder; and
   means for detachably securing the receptacle to the individual.

2. The case in claim 1 wherein the securing means comprises a waist belt.

3. The case in claim 2, wherein the flexible holder is longitudinally attached to the waist belt.

4. The case in claim 1, wherein the receptacle further comprises a layer of thermal insulation.

5. In combination, a medical device comprising a syringe and a protective case for said medical device, said protective case comprising:
   a receptacle for holding said device comprising a cavity capable of being sealed against moisture, dirt and contaminants;
   a removable cap for sealing said cavity; and
   a flexible holder for said receptacle.

6. The combination of claim 5 wherein said flexible holder is secured to a belt.

7. The combination of claim 5 wherein said receptacle includes an inner layer of insulation.

8. The combination of claim 5 wherein said removable cap is secured to said flexible holder.

9. The combination of claim 5 Wherein said receptacle is adhered to said flexible holder.

* * * * *